(12) United States Patent
Malessa

(10) Patent No.: US 7,998,379 B2
(45) Date of Patent: Aug. 16, 2011

(54) PROCESS FOR THE PRODUCTION OF POROUS MOULDED ARTICLES CONTAINING ALGINATE

(75) Inventor: Ralf Malessa, Essen (DE)

(73) Assignee: Dr. Suwelack Skin & Health Care AG, Billerbeck (DE)

( * ) Notice: Subject to any disclaimer, the term of this patent is extended or adjusted under 35 U.S.C. 154(b) by 494 days.

(21) Appl. No.: 11/569,286

(22) PCT Filed: May 13, 2005

(86) PCT No.: PCT/EP2005/052203
§ 371 (c)(1),
(2), (4) Date: Dec. 29, 2006

(87) PCT Pub. No.: WO2005/113656
PCT Pub. Date: Dec. 1, 2005

(65) Prior Publication Data
US 2007/0218285 A1    Sep. 20, 2007

(30) Foreign Application Priority Data

May 21, 2004   (DE) .................... 10 2004 025 495

(51) Int. Cl.
*B29C 67/20*   (2006.01)
*B29C 35/02*   (2006.01)
*C08J 9/26*    (2006.01)
*B05B 3/00*    (2006.01)
*F26B 5/06*    (2006.01)

(52) U.S. Cl. .............. 264/49; 264/28; 34/284

(58) Field of Classification Search .......... 264/42–44, 264/51
See application file for complete search history.

(56) References Cited

U.S. PATENT DOCUMENTS

| 3,060,032 A | * | 10/1962 | Glicksman .............. 426/575 |
| 3,653,383 A | * | 4/1972 | Wise ..................... 604/364 |
| 5,718,916 A | * | 2/1998 | Scherr ................... 424/445 |
| 5,851,461 A | * | 12/1998 | Bakis et al. ............. 264/50 |
| 5,925,009 A | * | 7/1999 | Mahoney et al. ........ 602/44 |
| 5,977,188 A | * | 11/1999 | Okamoto et al. ........ 514/738 |

FOREIGN PATENT DOCUMENTS

| CA | 2383523 | | 3/2001 |
| DE | 4328329 | | 3/1994 |
| DE | 20219666 U | | 2/2003 |
| GB | 560317 | | 3/1944 |
| GB | 621230 | | 4/1949 |
| GB | 2357765 | | 7/2001 |
| JP | 02208332 A | * | 8/1990 |
| WO | 84/02255 | | 6/1984 |
| WO | 94/00512 | | 1/1994 |
| WO | 95/12632 | | 5/1995 |
| WO | 2004104076 A1 | | 12/2004 |

OTHER PUBLICATIONS

Translation of JP 02-208322 A.*
Flink et al., "A Novel Method for Immobilization of Yeast Cells in Alginate Gels of Various Shapes by Internal Liberation of Ca-Ions," Biotechnology Letters vol. 7, No. 10, pp. 765-768, 1985.
Japanese Patent Abstract Publication No. 02208332, published Aug. 17, 1990, "Production of Polymeric Porous Material," one page.
International Search Report for PCT/EP2005/052203 dated Aug. 18, 2005, four pages.
English translation of International Preliminary Report for PCT/EP2005/052203 dated May 13, 2005, six pages.
Römpp Online, Version 3.4, "komplexbildende Polymere," Aug. 2008, three pages.

* cited by examiner

*Primary Examiner* — Christina Johnson
*Assistant Examiner* — Benjamin Schiffman
(74) *Attorney, Agent, or Firm* — Rankin, Hill & Clark LLP

(57) ABSTRACT

The invention relates to a process for the production of alginate-containing porous or sponge-like moulded articles, and to the moulded articles obtainable thereby and their use.

27 Claims, No Drawings

PROCESS FOR THE PRODUCTION OF POROUS MOULDED ARTICLES CONTAINING ALGINATE

PRIOR ART

The invention relates to processes for the production of porous or sponge-like moulded articles containing alginate, and to the moulded articles obtainable thereby and their use.

It is known that alkali alginates, for example Na alginate, are water-soluble whereas alkaline earth alginates, for example Ca alginate, are insoluble in water. Thin, water-insoluble layers can therefore be produced, for example, by spraying a thin Na alginate film with a $CaCl_2$ solution. If, on the other hand, it is desired to produce thicker layers, the difficulty is that the homogeneous incorporation of free Ca ions into a Na alginate solution is made more difficult by a pronounced increase in the solution viscosity, so that the resulting products are not uniform products but incoherent Ca alginate agglomerates.

In order to overcome this problem, U.S. Pat. No. 5,718,916 proposes, for example, adding a water-soluble complexing agent, for example sodium citrate, to the aqueous solution of the water-soluble alginate composition. If, for example, a readily soluble calcium salt such as calcium chloride is subsequently added, the immediate precipitation of calcium alginate is retarded by the presence of the complexing agent, as a result of which the formation of insoluble calcium alginate spherules in the product is said to be prevented. However, the examples of the mentioned US patent specification work on scales of a few millilitres. The gelling time of the alginate solution after addition of the calcium chloride is only from 30 to 60 seconds. When attempts are made to transfer this process to larger scales it is found that the desired retardation by addition of the complexing agent to the solution of sodium alginate is inadequate, and it is not possible to obtain a relatively large-sized product with high homogeneity. Furthermore, the use of surface-active agents is obligatory in the mentioned process in order to achieve adequate dispersion of the components. However, the use of such surface-active agents can lead to intolerances, for example on application to the skin. The fact that adequate retardation of precipitation is not achieved in the process of U.S. Pat. No. 5,718,916 by the prior addition of the complexing agent is also confirmed in GB 2357765 of the same inventor, wherein the process of U.S. Pat. No. 5,718,916 is consequently described as disadvantageous. GB 2357765 discloses a process for the production of water-insoluble alginate sponges or foamed products for the production of adhesive plasters or surgical products, in which process water-soluble alginate is likewise crosslinked in the presence of a foam-forming agent by the addition of polyvalent metal ions. A complexing agent is deliberately omitted in this process. In a preferred variant, the process is carried out in the presence of ammonium hydroxide in order to lower the viscosity of the calcium alginate. In the examples, calcium sulfate, for example, and then acetic acid are added. The process requires the presence of a foam-forming agent, surface-active agents, a borate buffer and the mentioned ammonium compounds. This complex mixture of substances makes the process difficult to control, and the resulting products contain a plurality of components whose physiological actions must be taken into consideration.

DE 202 19 666 U1 describes pads for dermatological applications, which pads comprise a carrier material based on a polymer, especially based on alginic acid. Concrete examples of the production of these pads are not to be found in this utility model.

DE 43 28 329 further discloses freeze-dried biomatrices for moisturising the skin and for the topical transdermal administration of pharmaceutical active ingredients having cosmetic activity, which biomatrices comprise natural polysaccharides and modified polysaccharides. This specification also already mentions stabilising the biomatrix by the formation of calcium alginate structures by the addition of calcium ions. This publication does not indicate how to produce thicker homogeneous alginate layers.

The production of small-sized alginate sponges for oral ingestion by adding a soluble calcium salt (calcium gluconate) to Na alginate solution is described in WO 01/17377. However, this process is unsuitable for the production of large-sized alginate sponges for the reasons already mentioned above (incorporation of the calcium ions is not homogeneous). Furthermore, loading with active ingredients, as proposed therein, is made more difficult by the resulting inhomogeneities.

A process for the formation of polysaccharide sponges, especially based on alginate, is known from WO 94/00512. In one embodiment, this patent specification also discloses a variant in which an insoluble carbonate or hydrogen carbonate salt of polyvalent metal cations is dispersed in the foamed polysaccharide and the foam is subsequently treated with a strong acid in order to free carbon dioxide and, as a result of the cations that form, crosslink the polysaccharide with the formation of a foamed structure having dimensional stability. According to information in the publication, foam thicknesses of up to 5 mm can be stabilised in this manner. However, such thicknesses are inadequate especially when it is desired subsequently to cut the foamed moulded articles into thinner layers. Moreover, the use of calcium carbonate leads to the (desirable) formation of gas during production, with the result that the pore sizes can scarcely be controlled and pronounced inhomogeneities in the foam result.

A further process for the production of alginate sponges is known from U.S. Pat. No. 3,653,383. In this process, Ca alginate is first prepared from alginic acid and calcium carbonate; the Ca alginate formed is then comminuted, and the resulting gel is subjected to freeze-drying. Although relatively large-sized foam-like materials can be produced in this manner, the resulting products disintegrate relatively rapidly in water. The wet strength, especially the wet tenacity, of the alginate sponges—especially when cut into thin layers—is accordingly inadequate for cosmetic or medical pads.

German Patent Application DE 10323794.1, which has not yet been published, describes a process for the production of porous alginate moulded articles which requires the addition of complexing agents for polyvalent metal ions or of a salt of a polyvalent metal ion with a polydentate complexing anion. The use of calcium sulfate and a mineral acid in the production of the porous alginate moulded articles is not taught.

Accordingly, the object of the present invention was to provide relatively large-sized, highly homogeneous moulded articles based on compounds of alginates and polyvalent metal ions, which moulded articles have high wet strength, in particular high wet tenacity, can be cut into thin layers with conventional cutting devices, are visually pleasing, i.e. especially have a high degree of whiteness, and can accordingly be used for cosmetic or medical applications, for example as cosmetic skin pads or as medical pads for wounds, etc. Furthermore, the process for the production of the moulded articles should be simple to control and should dispense as far as possible with the use of physiologically unacceptable additives such as foam-forming agents, surface-active agents, borate buffers and ammonium compounds.

It should furthermore permit the provision of homogeneous, thick, porous alginate layers from which there can be produced in a simple manner, by compression and/or punching out, suitable, including orally administrable, cosmetic or medical forms of administration, for example moulded articles for implants, compressed satiating products, agents for the controlled, especially delayed, release of active ingredients or the like.

The inventors of the present patent application have, surprisingly, succeeded in providing homogeneous, relatively thick, large-sized moulded articles based on alginates of polyvalent metal salts, which moulded articles can be produced by the special process to which this invention also relates, which solve the above problems associated with the moulded articles of the prior art, and which are therefore outstandingly suitable for the production of cosmetic or medical products. The moulded articles preferably contain neither foam-forming agents nor surface-active agents nor borate buffers nor ammonium compounds.

DETAILED DESCRIPTION OF THE INVENTION

The present patent application accordingly provides a process for the production of porous moulded articles containing alginate, which process comprises mixing an aqueous alginate solution with calcium sulfate in the presence of at least one mineral acid, pouring the resulting mixture into a mould and drying the mixture. Examples of mineral acids include hydrochloric acid, sulfuric acid and phosphoric acid. Hydrochloric acid is preferred.

The water-soluble alginates used according to the invention are preferably alkali metal alginates, such as alginates of sodium, potassium, etc.

The underlying alginic acid is a natural acidic polysaccharide which is extracted especially from so-called brown algae (Phaecophyceae) having a high molecular weight varying approximately from 30,000 to 200,000 daltons and which contains chains formed of D-mannuronic and L-guluronic acid. The degree of polymerisation varies in dependence on the type of alga used for the extraction, the season in which the algae were collected and the site of origin of the algae, as well as the age of the plants. The main species of brown algae from which alginic acid is obtained are, for example, *Macrocystis pyrifera, Laminaria cloustoni, Laminaria hyperborea, Laminaria flexicaulis, Laminaria digitata, Ascophyllumnodosum* and *Fucus serratus*. Alginic acid or alkaline alginates can, however, also be obtained microbiologically, for example by fermentation with *Pseudomonas aeruginosa* or mutants of *Pseudomonas putida, Pseudomonas fluorescens* or *Pseudomonoas mendocina* (see e.g. EP-A-251905 and Römpp Chemie Lexikon "Naturstoffe" Thieme Verlag, 1997 and documents cited therein).

Preference is given according to the invention to alginates having an average particle size of up to about 0.2 mm and a viscosity in aqueous solution (1% solution, pH 7, 20° C.) of from 300 to 800 mPas.

Particular preference is given according to the invention to sodium alginate.

The concentration of the aqueous solution of the water-soluble alginate used is preferably such that the concentration of alginate established in the aqueous suspension formed after addition of the calcium sulfate and the mineral acid is from 0.2 to 3.0%, more preferably from 0.3 to 2.5%, even more preferably from 0.4 to 1.2% (wt./wt.), based on the amount of water used. The solution can be prepared by suspending the desired amount of alginate in, for example, distilled water. The concentration of alginate in the aqueous suspension affects the hardness of the porous moulded articles that are formed. Concentrations of more than 2% (w/w) result in relatively hard or brittle moulded articles, which is less preferred. Concentrations less than 2% (w/w) result in less brittle moulded articles, which is more preferable.

In a further preferred embodiment, the porous moulded articles according to the invention comprise carboxymethylcellulose, especially sodium carboxymethylcellulose. The addition of sodium carboxymethylcellulose surprisingly leads to an improvement in the optical density of the porous moulded articles according to the invention without increasing the hardness or brittleness of the moulded articles. On the contrary, the addition of sodium carboxymethylcellulose leads to an improvement in the flexibility of the resulting porous moulded articles. Furthermore, the addition of carboxymethyl-cellulose, especially sodium carboxymethylcellulose, leads to stabilisation of the moulded articles. In the production of carboxymethylcellulose-containing moulded articles, the carboxymethylcellulose, especially sodium carboxymethylcellulose, surprisingly also prevents sedimentation of the sparingly soluble salt, especially $CaSO_4$, and accordingly enables it to be incorporated more homogeneously into the aqueous suspension and permits an increase in the homogeneity of the resulting moulded articles. In a preferred embodiment of the process according to the invention, therefore, a suspension of $CaSO_4$ and sodium carboxymethylcellulose is formed in water, and the aqueous sodium alginate solution, which contains the mineral acid and optionally further ingredients, as described hereinbelow, is added thereto.

Carboxymethylcellulose, especially sodium carboxymethylcellulose, can be present in the moulded articles according to the invention in an amount of up to 90 wt. %, based on the dry content of the moulded article. This corresponds to the establishment in the aqueous suspension of preferred ranges of approximately up to 3 wt. %, preferably from 0.2 to 3 wt. %.

A preferred embodiment of the moulded article according to the invention comprises carboxymethylcellulose, especially sodium carboxymethylcellulose, and hyaluronic acid or salts or derivatives thereof.

In the process according to the invention it is in principle also possible to add a complexing agent for calcium in order to lower the concentration of calcium ions in the solution and accordingly inhibit crosslinking of the alginate, although this is not absolutely necessary. Such a complexing agent may be a carboxylate of an α-hydroxypolycarboxylic acid, such as a citrate or malate, but which may serve as a constituent having cosmetic activity, for example as a skin moisturising agent.

According to the invention it is found, surprisingly, that the pH value established by the mineral acid has an effect on the tear strength of the resulting porous moulded articles. In order to achieve a higher tear strength, a pH value of less than 6, more preferably less than 5, is therefore preferred. Such low pH values are in turn particularly preferred in combination with a low alginate concentration of less than 2% (w/w) in the resulting suspension.

The amount of $CaSO_4$ is advantageously so chosen that the concentration of the salt in the resulting suspension is approximately from 0.1 to 500 mmol./litre, which is here intended to mean the total amount of salt based on the volume of the suspension.

The amount of $CaSO_4$ added, based on the amount of soluble alginate in the solution, is preferably so chosen that the molar ratio of alginate to $CaSO_4$ is from 0.001 to 1.

The formation of the sparingly soluble alginates is advantageously so controlled that at least about one minute, preferably about 2 minutes, more preferably at least about 3 minutes, a flowability of the alginate solution, expressed as viscosity at room temperature (20° C.), of less than about 1000 mPas is permitted.

Mixing of the aqueous alginate solution, the calcium sulfate and at least one mineral acid can preferably be carried out in mixers having a stator/rotor system, for example in a colloid mill.

According to the invention, the (still) flowable alginate composition is poured into a desired mould for subsequent drying. Layer thicknesses of the flowable alginate composition of up to about 50 cm are possible. Preferred moulds are box-type moulds having a rectangular basic outline. Pouring can take place at any suitable stage of the process. Accordingly, it is possible to pour the solution of the water-soluble alginate into the later mould used for drying, if adequate mixing in that mould can be ensured. Preferably, however, pouring is carried out after crosslinking or precipitation of the sparingly soluble alginate has commenced.

Drying of the aqueous alginate suspension poured into the mould is carried out in a manner known per se. Freeze-drying is particularly preferred. This can likewise be carried out in a manner known per se, and reference may here be made, for example, to DE 4328329 C2 or DE 4028622 C2, to which express reference should be made in relation to the drying step of the process according to the invention and which accordingly form part of the process according to the invention.

In a preferred embodiment of the process according to the invention there is additionally carried out, before the suspension is poured into a mould, the addition of at least one further component selected from the group consisting of: cosmetic or medical active ingredients, further natural or synthetic hydrocolloid-forming polymers and cosmetic or medical auxiliary substances or additives.

Further natural or synthetic hydrocolloid-forming polymers include (in some cases) water-soluble, natural or synthetic polymers which form gels or viscous solutions in aqueous systems. They are advantageously selected from further natural polysaccharides, synthetically modified derivatives thereof or synthetic polymers. Examples of further polysaccharides include homoglycans or heteroglycans, for example carragheen, pectins, tragacanth, guar gum, locust bean flour, agar-agar, gum arabic, xanthan gum, natural and modified starches, dextrans, dextrin, maltodextrins, chitosan, glucans, such as $\beta$-1,3-glucan, $\beta$-1,4-glucan, such as cellulose, mucopolysaccharides, such as especially hyaluronic acid, etc. Examples of synthetic polymers include: cellulose ethers, polyvinyl alcohol, polyvinylpyrrolidone, synthetic cellulose derivatives, such as methylcellulose, carboxycellulose, carboxymethyl-cellulose, especially sodium carboxymethylcellulose, cellulose esters, cellulose ethers such as hydroxypropylcellulose, polyacrylic acid, polymethacrylic acid, poly (methyl methacrylate) (PMMA), polymethacrylate (PMA), polyethylene glycols, etc. It is also possible to use mixtures of these polymers. The use of hydrocolloid-forming proteins, for example collagen, is not preferred, however, because some end users increasingly prefer the use of purely plant products, especially in cosmetics.

Particular preference is given according to the invention to the addition of hyaluronic acid and/or salts thereof and/or derivatives thereof. Hyaluronic acid is a highly viscous, natural glucosaminoglycan with alternating $\beta_{1-3}$-glucoronic acid and $\beta_{1-4}$-glucosamine components; its molecular weight is from 50,000 to several million. Hyaluronic acid is frequently used in the form of the sodium salt, e.g. in therapy, principally in ophthalmology, surgery and cosmetics. The salts of hyaluronic acid formed with alkali, alkaline earth, magnesium, aluminium, ammonium or substituted ammonium ions can be used as carriers for increasing the absorption of medicaments (see e.g. Römpp Chemie Lexikon "Naturstoffe" Thieme Verlag, 1997 and documents cited therein). Particular preference is given according to the invention to sodium hyaluronate having a molecular weight of approximately from 1,000,000 to 2,500,000 daltons. The addition of hyaluronic acid in the process according to the invention surprisingly leads to increased whiteness of the resulting porous moulded articles containing alginate. This is very preferred for aesthetic reasons, especially in cosmetic applications. However, hyaluronic acid additionally develops its therapeutic activity, e.g. moisturisation of the skin or promotion of the healing of wounds, especially in the case of topical or external application.

Hyaluronic acid or salts thereof is/are added to the alginate-containing porous moulded articles according to the invention in an amount, based on the dried moulded article, of approximately from 0.1 to 90 wt. %, preferably from 1 to approximately 67 wt. %.

Active ingredients added according to the invention include especially cosmetic or therapeutic or pharmaceutical active ingredients, in particular active ingredients suitable for external application. The moulded article produced according to the invention preferably comprises at least one cosmetic and/or pharmaceutical active ingredient. Accordingly, the moulded articles to which preference is given according to the invention are preferably cosmetic or therapeutic agents. Within the scope of the invention, cosmetic moulded articles, or moulded articles produced using cosmetic active ingredients, are substantially agents within the meaning of the Lebensmittel-und Bedarfsgegenständegesetz (food and commodities law—LMBG), i.e. substances or preparations of substances which are intended to be applied externally to humans for the purpose of cleansing, care or for influencing the appearance or body odour, or for imparting impressions of smell, unless they are intended predominantly for alleviating or eliminating diseases, illness, injuries to the body or pathological disorders. In this sense, the cosmetic moulded articles produced according to the invention are, for example, cosmetic pads, for example face masks, etc., which may be used, for example, as skin washing and cleansing agents, skin care agents, especially facial skin care agents, cosmetics for the eyes, lip care agents, nail care agents, foot care agents and also as hair care or dental hygiene agents.

Examples of compounds having cosmetic, optionally also, for example, dermatological, and therapeutic activity include: anti-acne agents, antimicrobial agents, antiperspirants, astringents, deodorants, hair-removing agents, conditioning agents for the skin, skin-smoothing agents, agents for increasing the hydration of the skin, for example glycerin or urea, sun protection agents, keratolytics, radical acceptors for free radicals, antiseptic active ingredients, active ingredients for treating the signs of skin ageing and/or agents which modulate the differentiation and/or proliferation and/or pigmentation of the skin, vitamins such as vitamin C, active ingredients having a stimulating side-effect, such as alpha-hydroxy acids, $\beta$-hydroxy acids, alpha-keto acids, $\beta$-keto acids, retinoids (retinol, retinal, retinic acid), anthralins (dioxyanthranol), anthranoids, peroxides (especially benzoyl peroxide), minoxidil, lithium salts, antimetabolites, vitamin D and its derivatives; catechols, flavonoids, ceramides, fatty substances, such as mineral oils, such as paraffin oils or Vaseline oils, silicone oils, vegetable oils such as coconut oil, oil of sweet almonds, apricot oil, corn oil, jojoba oil, olive oil, avocado oil, sesame oil, palm oil, eucalyptus oil, rosemary oil, lavender oil, pine oil, thyme oil, mint oil, cardamom oil, orange blossom oil, soybean oil, bran oil, rice oil, rape oil and castor oil, wheatgerm oil and vitamin E isolated therefrom, evening primrose oil, plant lecithins (e.g. soya lecithin), sphingolipids/ceramides isolated from plants, animal oils or fats, such as tallow, lanolin, clarified butter, fatty acid esters, esters of fatty alcohols and waxes having a melting point corresponding to the temperature of the skin (animal waxes, such as beeswax, carnauba wax and candelilla wax, mineral waxes, such as microcrystalline waxes, and synthetic waxes, such as polyethylene or silicone waxes), as well as all oils suitable for cosmetic purposes, as mentioned, for example, in CTFA transactions, Cosmetic Ingredient Handbook, 1st Edition, 1988, The Cosmetic, Toiletry and Fragrance Association, Inc., Washington, polyunsaturated fatty acids, essential fatty acids (e.g. gamma-linolenic acid), enzymes, coenzymes, enzyme inhibitors, hydrating agents, skin-calming agents, detergents or foam-forming agents, and inorganic or synthetic delustering fillers, abrasive agents.

Mention may also be made of plant active ingredient extracts, or extracts or individual substances obtained therefrom, which can be added to the porous moulded articles produced according to the invention. In general, the plant active ingredient extract is usually selected from the group consisting of solid plant extracts, liquid plant extracts, hydrophilic plant extracts, lipophilic plant extracts, individual constituents of plants; and mixtures thereof, such as flavonoids and their analogues; rutin, quercertin, diosmin, hyperoside, (neo)hesperidine, hesperitin, ginkgo biloba (e.g. ginkgoflavone glycosides), crataegus extract (e.g. oligomeric procyanidines), buckwheat (e.g. rutin), Sophora japonica (e.g. rutin), birch leaves (e.g. quercertin glycosides, hyperoside and rutin), elder blossom (e.g. rutin), linden blossom (e.g. essential oil with quercertin and farnesol), hypericon oil (e.g. olive oil extract), calendula, arnica (e.g. oily extracts of the blossom with essential oil, polar extracts with flavonoids), melissa (e.g. flavones, essential oil); immune stimulants: Echinacea purpurea (e.g. alcoholic extracts, fresh sap, pressed juice), Eleutherokokkus senticosus; alkaloids: rauwolfia (e.g. prajmaline), evergreen (e.g. vincamine); further phytopharmaceuticals: aloe, horse chestnut (e.g. aescin), garlic (e.g. garlic oil), pineapple (e.g. bromelains), ginseng (e.g. ginsenosides), milk thistle fruits (e.g. extract standardised to silymarin), butcher's broom root (e.g. ruscogenin), baldrian (e.g. valepotriate, Tct. valerianae), kava kava (e.g. kavalactones), hop blossom (e.g. hop bitters), extr. passiflorae, gentian (e.g. ethanol. extract), anthraquinone-containing drug extracts, e.g. aloin-containing aloe vera juice, pollen extract, algae extracts, liquorice root extracts, palm extract, galphimia (e.g. mother tincture), mistletoe (e.g. aqueous-ethanol. extract), phytosterols (e.g. beta-sitosterol), mullen flowers (e.g. aqueous-alcohol. extract), drosera (e.g. liqueur wine extract), sea buckthorn fruits (e.g. juice extracted therefrom or sea buckthorn oil), marshmallow root, primrose root extract, fresh plant extracts from mallow, comfrey, ivy, horsetail, yarrow, ribwort (e.g. pressed juice), stinging nettle, celandine, parsley; plant extracts from Norolaena lobata, Tagetes lucida, Teeoma siems, Momordica charantia, and aloe vera extracts.

Preferred cosmetic active ingredients are natural and synthetic humectants, for example glycerin, urea and ceramides, skin-protecting agents, skin-lightening agents, vitamins, antioxidants, so-called anti-ageing agents, anti-irritants, sun-protection agents, etc.

Further preferred cosmetic active ingredients are natural fats and oils, i.e. triglycerides of natural fatty acids, for example on account of their re-moisturising and caring action on the skin.

A particularly preferred cosmetic active ingredient is urea, which is assumed also to act as a local anaesthetic.

In contrast to the above-described moulded articles used substantially in cosmetics, the moulded articles used therapeutically (medicaments/medical products) are preferably those that comprise at least one pharmaceutical or therapeutic active ingredient, especially also a dermatological active ingredient, and that, within the meaning of the medicaments law, are intended inter alia for healing, alleviating or protecting against diseases, illness, injuries to the body or pathological disorders. Alginate itself can, however, also be regarded as such a pharmaceutically/therapeutically active constituent. The agents or active ingredients are intended for external application, and they may be active ingredients that have an action on the skin, as well as transdermal active ingredients. They include, for example: agents for the treatment of skin diseases, externally applicable analgesics, e.g. dextropropoxyphene, pentazocine, pethidine, buprenorphine; antirheumatics/antiphlogistics (NSAR), e.g. indomethacin, diclofenac, naproxen, ketoprofen, ibuprofen, flurbiprofen, salicylic acid and derivatives thereof, such as acetylsalicyclic acid, oxicams; steroid hormones, e.g. betamethasone, dexamethasone, methylprednisolone, ethinyloestradiol, medroergotamine, dihydroergotoxin; gout remedies, e.g. benzbromarone, allopurinol; external dermatics, including antibacterial agents, antimycotics, antiviral active ingredients, antiinflammatory active ingredients, anti-itch active ingredients, anaesthetising active ingredients, e.g. benzocaine, corticoids, acne agents, antiparasitic active ingredients; externally applicable hormones; venous therapeutic agents; immune suppressants, etc., all for external application.

Preferred therapeutic agents are analgesics, e.g. immune suppressants, hormones, agents for the treatment of skin diseases, such as neurodermitis, atopic dermatitis, etc., and anti-herpes agents.

The porous moulded articles produced according to the invention may optionally further comprise one or more auxiliary substances. Auxiliary substances include: fillers, agents for adjusting the pH, such as buffers, stabilisers, co-solvents, colourings and pigments for pharmaceutical and cosmetic use, or other colourings and pigments, preservatives, plasticisers, lubricants or glidants, etc. A particularly preferred auxiliary substance is squalane. Squalane has a skin-calming and skin-smoothing action.

By means of the present invention it is possible to produce porous moulded articles containing alginates of polyvalent metal ions, which moulded articles have a thickness of at least one centimetre, preferably at least 2 cm, and are obtained by crosslinking (or precipitating) alginate-containing aqueous solutions with salts of polyvalent metal ions and subsequently drying the aqueous suspension of the resulting crosslinked alginate. The thickness of the moulded article means the shortest distance between 2 points in such a moulded article. It was hitherto not possible in the prior art to produce such thick, large-sized moulded articles having the desired wet strength, especially wet tenacity, cuttability etc. These porous moulded articles are preferably obtained by the process according to the invention. The processes that comprise the freeze-drying of comminuted insoluble alginates lead to porous or sponge-like materials that readily disintegrate and are unsuitable for the use intended herein.

When 1 g of the moulded article is suspended in 100 g of water at 20° C., the porous moulded articles according to the invention have a pH value of the aqueous phase of less than 7, preferably less than 6. Such an acidic pH value is preferred especially in the case of cosmetic application to the skin.

The porous moulded article according to the invention preferably has a density of from 0.005 to 1 g/cm$^3$, preferably from 0.01 to 0.5 g/cm$^3$ (determined in accordance with DIN 53420).

The porous moulded article according to the invention preferably has a wet tenacity of at least about 10 mN/mm layer thickness (determined in accordance with DIN 53328).

The porous moulded articles according to the invention do not consist or substantially do not consist of spun alginate fibres, for example calcium alginate fibres.

As mentioned above, the mentioned porous moulded articles according to the invention may additionally comprise at least one further component selected from the group consisting of: cosmetic or medical active ingredients, further natural or synthetic hydrocolloid-forming polymers and cosmetic or medical auxiliary substances or additives. These may be contained in the porous moulded articles according to the invention in amounts of up to 0.75 g/g, preferably less than 0.5 g/g of the moulded article.

The porous moulded articles according to the invention are outstandingly suitable for the production of moulded articles in layer form, by cutting the porous moulded articles according to the invention in a manner known per se. This is not possible, for example, with the sponge-like materials produced by the freeze-drying of comminuted insoluble alginates. Cutting of the porous moulded articles according to the invention yields, for example, layer thicknesses of from 0.5 to 20 mm. The invention relates also to the porous moulded articles in layer form so obtained. Such porous moulded articles in layer form are suitable especially for external application, for example as a cosmetic or medical pad, as a wound-dressing material, as a pad for wounds, as an implant material, as a cell culture matrix, etc.

The porous moulded articles according to the invention are also outstandingly suitable for the production of compressed, expandable sponge-like moulded articles, as are described, for example, in EP 0901792 of the Applicant on a collagen basis. They can be produced in a simple manner from the large-sized porous moulded articles, especially the large-sized porous moulded articles obtained after freeze-drying, by punching out and/or compression, especially also on an industrial scale, which has not readily been possible hitherto by the methods of the prior art.

Such compressed articles are suitable especially for oral, buccal or nasal application, for example as compressed satiating products, which may optionally contain additional active ingredients, food supplements or vitamins (e.g. DE 19942417).

Owing to the sparingly soluble nature of the porous moulded articles according to the invention they are further suitable for the production of forms that are loaded with active ingredient, from which the active ingredient is released in a controlled manner, especially in a delayed manner. Such forms include both sponges containing active ingredient, such as implants, vaginal suppositories as well as orally administrable forms, the latter especially in the form of compressed products which expand in the wetted state, such as in the stomach, to a multiple of their compressed volume and release the active ingredient they contain from the sponge-like matrix (e.g. WO 98/09617).

The present invention relates further to porous moulded articles containing alginates of polyvalent metal ions and hyaluronic acid and/or salts thereof and/or derivatives thereof, which moulded articles are obtained by the process according to the invention. These moulded articles, as already described above, surprisingly have increased whiteness, which is very preferred for cosmetic applications in particular, but also for medical applications. With regard to the composition of such hyaluronic-acid-containing porous moulded articles, reference may be made, for example, to the above comments. The hyaluronic-acid-containing porous moulded articles are preferably produced by the process according to the invention.

The present invention relates further to the use of the porous moulded articles according to the invention, or of the moulded articles obtained by the process according to the invention, as cosmetic agents.

When used in cosmetics, the porous moulded articles according to the invention are preferably used in the form of cosmetic skin pads, which are applied in the moistened state to the skin and are removed again after a specific action time, for example after absorption of the active ingredients contained therein. The alginate itself also develops a cosmetic action, such as hydration and smoothing of the skin.

The present invention relates further to the use of the porous moulded articles according to the invention, or of the moulded articles obtained by the process according to the invention, in the production of a medical product. Such medical products include, for example, pads for wounds, transdermal pads, adhesive plasters, implants, substrates for the culturing of cells, agents for the controlled, especially delayed, administration of active ingredients in the form of said implants, as well as orally administrable retard preparations, or in the form of so-called compressed satiating products, which produce a feeling of fullness by expansion of the compressed porous moulded article in the stomach. The latter can also be loaded with food supplements, vitamins, minerals or other active ingredients.

The porous moulded articles according to the invention, or the moulded articles obtained by the process according to the invention, are preferably used for external application, such as especially in the form of a cosmetic or medical pad. In addition, however, as mentioned, application orally, buccally, vaginally, nasally, etc. is also possible, for example. The homogeneous, thick, porous alginate moulded articles obtainable according to the invention permit, as stated, the production of any of these forms of application on an industrial scale using known methods, such as cutting, pressing or compression and/or punching out.

Particularly preferred moulded articles according to the invention comprise, based on dry substance, that is to say without residual moisture:
approximately from 6 to 100 wt. % alginate,
from 0 to approximately 90 wt. % carboxymethylcellulose, especially the sodium salt thereof,
from 0 to approximately 70 wt. % hyaluronic acid or salts or derivatives thereof,
from 0 to approximately 90 wt. % natural or synthetic oils,
from 0 to approximately 70 wt. % citric acid or salts thereof, which corresponds to preferred contents in the aqueous suspension to be freeze-dried in step c) of
approximately from 0.2 to 3 wt. % alginate,
from 0 to approximately 3 wt. % carboxymethylcellulose, especially the sodium salt thereof,
from 0 to approximately 1 wt. % hyaluronic acid or salts or derivatives thereof,
from 0 to approximately 3 wt. % natural or synthetic oils,
from 0 to approximately 1 wt. % citric acid or salts thereof.

The porous moulded articles according to the invention are preferably in the form of a layer, i.e. the length and width of the moulded article are at least 10 times, preferably at least 20 times, as great as the thickness of the moulded article. Such layers can also be cut into shapes, for example into the shape of a face mask. The layers have a surface area of preferably at least about 25 cm², more preferably at least about 50 cm², yet more preferably of at least about 100 cm².

The invention further relates also to laminates containing at least one layer, as described above, which is laminated on at least one side with at least one further carrier layer. The layer according to the invention is preferably laminated on only one side with preferably only one carrier layer. The carrier layer preferably consists of a rayon net (of viscose). Such laminates are used preferably as a wound pad or an adhesive plaster and particularly preferably as a cosmetic mask.

The invention relates also to a combination containing at least one of the porous moulded articles according to the invention and at least one aqueous solution comprising one or more active ingredients and/or auxiliary substances, in a coherent spatial arrangement (application packet, set, kit-of-parts etc.). The active ingredient solution may be, for example, solutions of readily volatile active ingredients and/or auxiliary substances which, owing to the production process by freeze-drying, should not or cannot be incorporated into the moulded article, such as, for example, certain fractions of essential oils, perfumes, etc. The solution may also contain temperature-sensitive pharmaceutical or cosmetic active ingredients.

The invention is explained in greater detail with reference to the following example.

EXAMPLE 1

Step 1

| | |
|---|---|
| 2500 g | RO water (demineralised water, reverse osmosis) |
| 32.5 g | Na alginate |
| 10.0 g | citric acid |
| | HCl |

Incorporate the alginate powder and the citric acid into the RO water by means of a mixer until a homogeneous mixture is formed. HCl is then added. (Optional cosmetic and/or medical active ingredients and/or oils or other substances, etc. can advantageously also be incorporated into this mixture at this point).

Step 2

| | |
|---|---|
| 50 g | RO water |
| 10.0 g | calcium sulfate |
| 10.0 g | sodium carboxymethylcellulose |

The calcium sulfate and the sodium carboxymethylcellulose are added to 50 ml of RO water, with stirring.

Step 3

The solutions from step 1 and step 2 are mixed intimately for about 30 seconds.

Step 4

The mixture from step 3 is poured into a mould and left for about 1 hour to complete the reaction.

Step 5

The gelled moulded article is cryotransferred and freeze-dried.

Step 6

The freeze-dried, large-sized, porous or sponge-like moulded article, optionally containing additional substances, can be produced as discussed above.

The invention claimed is:

1. A process for the production of freeze-dried porous molded articles comprising:
    (a) mixing an aqueous alginate solution with at least one mineral acid until a pH of less than 6 is established,
    (b) subsequently adding a component comprising calcium sulfate,
    (c) pouring the resulting mixture into a mold and
    (d) subsequently freeze-drying the resulting cross-linked alginate-mixture,
wherein the process excludes the addition of foam-stabilizing agents.

2. The process according to claim 1, wherein the mineral acid is hydrochloric acid.

3. The process according to claim 1, wherein the aqueous alginate solution is the aqueous solution of an alkali metal alginate.

4. The process according to claim 1, wherein the component of (b), further comprises carboxymethylcelluose or a salt thereof.

5. The process according to claim 1, wherein the component of (b) further comprises sodium carboxymethylcellulose.

6. The process according to claim 1, further comprising after (a), and before (b), adding a complexing agent for calcium.

7. The process according to claim 6, wherein the complexing agent is a carboxylate of an α-hydroxypolycarboxylic acid.

8. The process according to claim 7, wherein the complexing agent is a citrate or malate of an α-hydroxypolycarboxylic acid.

9. The process according to claim 1, further comprising before freeze-drying, adding at least one further component selected from the group consisting of: cosmetic or medical active ingredients; natural or synthetic hydrocolloid-forming polymers; and cosmetic or medical auxiliary substances or additives.

10. The process according to claim 9, wherein the further component is at least one natural polysaccharide or a modified derivative thereof.

11. The process according to claim 9, wherein the further component is hyaluronic acid or a salt thereof.

12. The process according to claim 9, wherein the further component is urea or glycerin.

13. The process according to claim 9, wherein the further component is squalane, jojoba oil or triglycerides of natural fatty acids.

14. The process according to claim 9, wherein the further component is a vitamin.

15. The process according to claim 9, wherein the further component is an agent for the treatment of skin diseases or an antibacterial agent.

16. The process according to claim 1, wherein the addition of a salt of a polyvalent metal ion with a polydentate complexing anion is excluded.

17. The process according to claim 1, further comprising cutting the freeze-dried molded article into layer form.

18. The process according to claim 1, further comprising compressing the freeze-dried molded article into compressed form.

19. The process according to claim 18, wherein the compressed molded article is in the form of an orally administrable agent.

20. The process according to claim 18, wherein the compressed molded article is the form of an orally administrable satiating product.

21. The process according to claim 18, wherein the compressed molded article is in the form of an orally administrable agent for the controlled release of an active ingredient.

22. The process according to claim 1, wherein the pH value of the alginate solution, established by the mineral acid, is less than 5.

23. The process according to claim 1, wherein the concentration of the alginate in the aqueous solution is less than 2% (w/w) and the pH value of the alginate solution, established by the mineral acid, is less than 5.

24. The process according to claim 1, wherein the mixture is poured in a layer thickness of from 1 to 50 centimeters before freeze-drying.

25. The process according to claim 24, wherein the resulting freeze-dried molded articles are cut into layers of 0.5 to 20 mm thickness.

26. The process according to claim 1, wherein the concentration of the alginate in the aqueous solution is less than 2% (w/w) and the pH value of the alginate solution, established by the mineral acid, is less than 5, and wherein the resulting mixture is poured in a layer thickness of from 1 to 50 centimeters before freeze-drying.

27. A process for the production of freeze-dried porous molded articles comprising:
   (a) mixing an aqueous alginate solution with a concentration of less than 2% (w/w) with at least one mineral acid until a pH of less than 5 is established,
   (b) subsequently adding calcium sulfate,
   (c) pouring the resulting mixture in a layer thickness of at least one centimeter up to 50 centimeter thickness into a mold,
   (d) subsequently freeze-drying the resulting cross-linked alginate-mixture, and
   (e) cutting the resulting freeze-dried molded articles into layers of 0.5 to 20 mm thickness,
   wherein the process excludes the addition of foam-stabilizing agents.

* * * * *